(12) United States Patent
Jackson et al.

(10) Patent No.: US 6,797,278 B2
(45) Date of Patent: Sep. 28, 2004

(54) ANTIMICROBIAL SOL-GEL FILMS COMPRISING SPECIFIC METAL-CONTAINING ANTIMICROBIAL AGENTS

(75) Inventors: Delwin Jackson, Duncan, SC (US); Leland G. Close, Spartanburg, SC (US)

(73) Assignee: Milliken & Company, Spartanburg, SC (US)

( * ) Notice: Subject to any disclaimer, the term of this patent is extended or adjusted under 35 U.S.C. 154(b) by 12 days.

(21) Appl. No.: 10/036,652

(22) Filed: Dec. 21, 2001

(65) Prior Publication Data

US 2003/0118624 A1 Jun. 26, 2003

(51) Int. Cl.$^7$ .............................................. A01N 25/08
(52) U.S. Cl. .................. 424/409; 424/76.8; 424/78.09; 424/405; 424/411; 424/421; 424/618; 514/495
(58) Field of Search ................................ 424/405, 409, 424/411, 76.8, 78.09, 421, 617, 618; 514/492, 495

(56) References Cited

U.S. PATENT DOCUMENTS

| | | | | |
|---|---|---|---|---|
| 5,234,717 A | * | 8/1993 | Matsuno et al. | ............. 427/277 |
| 5,882,808 A | | 3/1999 | Oku et al. | .................. 428/699 |
| 2002/0005145 A1 | * | 1/2002 | Sherman | ..................... 106/436 |

FOREIGN PATENT DOCUMENTS

| US | 2002/0005145 A | * | 1/2002 |
|---|---|---|---|

* cited by examiner

Primary Examiner—Neil S. Levy
(74) Attorney, Agent, or Firm—Terry T. Moyer; Brenda D. Wentz

(57) ABSTRACT

Broadly defined sol-gel films for the coating of solid substrates, wherein such sol-gel films provide effective and durable antimicrobial properties. The utilization of such films permits relatively low-temperature production of antimicrobial substrates, such as ceramics, metals (e.g., stainless steel, brass, and the like), plastics (e.g., polyimides, polyamides, polyacrylics, and the like), glass (e.g., borosilicates, and the like), as compared with typical glazes for ceramics and the like. The inventive films comprise, as the primary antimicrobial active ingredients, certain metal-containing inorganic or organic antimicrobial compounds, such as, preferably, metal-containing ion-exchange, oxide, glass, sulfadiazine, and/or zeolite compounds (most preferably, including silver therein as the metal component). Preferably, also, the particular solid substrate to which such films are applied should exhibit substantially high melting and/or heat distortion temperatures to permit high temperature curing of the films to the solid substrate surface (in the range of 100–800° C., for example). If the solid substrate melts or distorts, the antimicrobial activity of the ultimate composite is drastically reduced. End uses for such film-coated articles include bathroom fixtures, appliances, kitchen articles and fixtures, furniture, glass, and any other surface that exhibits the high melt and/or heat distortion temperatures noted above and requires antimicrobial characteristics, including certain polymeric films. The specific method of producing such films is also encompassed within this invention.

15 Claims, No Drawings

ANTIMICROBIAL SOL-GEL FILMS COMPRISING SPECIFIC METAL-CONTAINING ANTIMICROBIAL AGENTS

FIELD OF THE INVENTION

This invention relates to broadly defined sol-gel films for the coating of solid substrates, wherein such sol-gel films provide effective and durable antimicrobial properties. The utilization of such films permits relatively low-temperature production of antimicrobial substrates, such as ceramics, metals (e.g., stainless steel, brass, and the like), plastics (e.g., polyimides, polyamides, polyacrylics, and the like), glass (e.g., borosilicates, and the like), as compared with typical glazes for ceramics and the like. The inventive films comprise, as the primary antimicrobial active ingredients, certain metal-containing inorganic or organic antimicrobial compounds, such as, preferably, metal-containing ion-exchange, oxide, glass, sulfadiazine, and/or zeolite compounds (most preferably, including silver therein as the metal component). Preferably, also, the particular solid substrate to which such films are applied should exhibit substantially high melting and/or heat distortion temperatures to permit high temperature curing of the films to the solid substrate surface (in the range of 100–800° C., for example). If the solid substrate melts or distorts, the antimicrobial activity of the ultimate composite is drastically reduced. End uses for such film-coated articles include bathroom fixtures, appliances, kitchen articles and fixtures, furniture, glass, and any other surface that exhibits the high melt and/or heat distortion temperatures noted above and requires antimicrobial characteristics, including certain polymeric films. The specific method of producing such films is also encompassed within this invention.

DISCUSSION OF THE PRIOR ART

All U.S. Patents listed below are herein entirely incorporated by reference.

There has been a great deal of attention in recent years given to the hazards of bacterial contamination from potential everyday exposure. Noteworthy examples of such concern include the fatal consequences of food poisoning due to certain strains of *Escherichia coli* being found within undercooked beef in fast food restaurants; Salmonella contamination causing sicknesses from undercooked and unwashed poultry food products; and illnesses and skin infections attributed to *Staphylococcus aureus, Klebsiella pneumoniae*, yeast, and other unicellular organisms. With such an increased consumer interest in this area, manufacturers have begun introducing antimicrobial agents within various household products and articles. For instance, certain brands of polypropylene cutting boards, liquid soaps, etc., all contain antimicrobial compounds. The most popular antimicrobial for such articles is triclosan. Although the incorporation of such a compound within liquid or certain polymeric media has been relatively simple, other substrates, including the surfaces of textiles and fibers, have proven less accessible. Furthermore, triclosan is a chlorinated compound which may, under certain conditions, release chlorine atoms from the substrate surface. Such ions are potentially hazardous to humans, due to skin irritation upon contact, as well as within environmental effluents, and the like. Additionally, harmful microbes have shown, on occasion, an ability to develop an immunity to the bactericidal properties of triclosan. Also, surface treatments with triclosan have proven ineffective as well since such compounds are easily washed from surfaces when topically applied thereto.

Thus, metal-containing (more specifically and preferably, specific silver-containing) inorganic microbiocides (e.g., ion-exchange, oxide, glass, sulfadiazine, and/or zeolite compounds) have recently been developed and/or utilized as antimicrobial agents on and within a plethora of different substrates and surfaces. In particular, such microbiocides have been adapted for incorporation within plastic compositions and fibers in order to provide household and consumer products which inherently exhibit antimicrobial characteristics. Although such silver-based agents provide excellent, durable, antimicrobial properties, to date no teachings exist which teach or fairly suggest the presence of such inorganic compounds within films or coatings (other than paints or other organically based coatings merely applied and not dried or cured at elevated temperatures thereto) for hard surface substrates, except for limited ceramic coatings as glaze components. These limited attempts at providing hard surface (e.g., ceramic) surface antimicrobial treatments to combat such potentially dangerous bacterial, fungal, etc., problems, have been limited to glazes for ceramic articles, such as within U.S. Pat. No. 5,882,808 to Oku et al. Such a glaze, although providing excellent antimicrobial activity to target ceramic substrates, also exhibits a serious drawback in that the use thereof is limited to ceramic surfaces, and that the temperatures required to cure and thus effectuate the adhesion of such a glaze to the target ceramic is very high (in the range of 1200° C.). Thus, in order to practice such an invention, there is a requirement for the generation of and exposure to such very high temperatures. From both safety and cost perspectives, there is thus a need to improve upon such a surface treatment. Furthermore, the development of a lower-temperature method of treating selected surfaces with durable antimicrobial coatings would also permit an expansion in the type of substrates to which such a coating or film may be applied. Basically, nothing has been disclosed or suggested that sol-gel coating films can provide improvements in terms of durable, low-temperature processing, articles, as discussed in greater detail below. Therefore, it remains highly desirable to provide a more versatile surface coating for hard surface substrates, particularly those that are consistently utilized for human hygienic and/or sanitation purposes (such as bathroom and/or kitchen fixtures; e.g., sinks, toilets, showers, and the like) that exhibits effective, and preferably durable, antimicrobial activity. To date, such a coating or film has heretofore been nonexistent within the pertinent prior art and industries.

DESCRIPTION OF THE INVENTION

It is thus an object of the invention to provide a low-temperature method of imparting a durable coating or film to certain hard surface substrates, such that the finished article exhibits excellent, durable, antimicrobial activity. Another object of the invention is to provide an antimicrobial hard surface substrate coated with a sol-gel film comprising at least one inorganic silver-based ion-exchange compound, oxide, or zeolite compound. Another object of the invention is to provide an antimicrobial sol-gel film that retains a high degree of antimicrobial activity in the presence of highly caustic solvents (and other standard cleaning agents) and that does not exhibit any aesthetically displeasing discolorations over time.

Accordingly, this invention encompasses an antimicrobial sol-gel film comprising at least one inorganic antimicrobial agent, wherein said film exhibits a log kill rate for *Klebsiella pneumoniae* of at least 0.5 (preferably, at least 1.5, more preferably, at least 2.5, and most preferably, at least 3.5) as measured under a modified plate contact method very similar to JIS Z2801:2000 (the Japanese Industrial testing protocol) utilizing a phosphate buffer solution instead of a dilute nutrient solution (as the simple modification). Furthermore, this invention also encompasses a hard surface substrate (such as ceramic, steel, brass, silica, glass, plastic)

that exhibits a melt and/or heat distortion temperature of at least 100° C., preferably, at least 200° C., more preferably at least 300° C., and most preferably at least 400° C., to which such an inventive sol-gel film as noted above has been applied. Also, this invention encompasses such a sol-gel film coated hard surface substrate exhibiting the same log kill rate as noted above after said substrate has been immersed in a heated caustic bath, having a pH level of at least 12, for 48 hours. Additionally, this invention encompasses a method of producing an antimicrobial hard surface substrate comprising the steps of a) providing a hard surface substrate; b) providing a sol-gel film precursor formulation comprising a host precursor and at least one metal-containing inorganically based antimicrobial agent; c) applying said sol-gel film precursor to at least a portion of said hard surface substrate; and d) exposing said coated hard surface substrate to a temperature of at most about 800° C. to form a finished sol-gel film-coated hard surface substrate, wherein said finished substrate exhibits a log kill rate for *Klebsiella pneumoniae* of at least 0.5 (with higher log kill rates preferred) as measured under a modified plate contact method similar to that pursuant to JIS Z2801:2000 (with, as noted above, the only difference being the utilization of a phosphate buffer solution instead of a dilute nutrient solution).

The term hard surface substrate is intended to encompass any hard surface to which a sol-gel film can effectively be applied, and thus that can withstand the temperatures required to effectively adhere such a film to such a surface. Such particular solid substrates to which the inventive sol-gel films may be applied should exhibit substantially high melting and/or heat distortion temperatures to permit high temperature curing of the films to the specific solid substrate surface (in the range of 100–800° C., for example). If the solid substrate melts or distorts, the antimicrobial activity of the ultimate composite is drastically reduced. In general, then, such a term encompasses such specific substrates as metals (such as, again, steel, stainless steel, brass, enameled metal, such as enameled steel, and the like, particularly metals utilized within or as the basis of bathroom fixtures, including wash basins, commodes, toilet stalls, sinks, pipes, countertops, and the like, as well as furniture, tableware, eating utensils, appliances, such as stoves, ovens, refrigerators, etc.), ceramics (including vitreous china, tiles, and the like, covering the same types of specific end-uses as for metals as noted above), plastics (e.g., polyimides, polyamides, polyacrylics, and other plastics that can withstand such requisite high temperatures, for the same end-use categories as listed above), glasses (e.g., silica, silicates, borosilicates, and the like, for various uses involving human contact). Thus, such a term is very broad in scope and is limited only to the required temperature ranges at which sol-gel films are properly applied to such surfaces. If the substrate melts or overly distorts in shape and/or constitution during sol-gel film application, then the substrate will not exhibit the desired antimicrobial activity, not to mention retain its desired shape thereafter, and thus is not encompassed within the definition of the term. Also, it is noted that this invention is limited in scope to articles treated with sol-gel films, and not to sol-gel composites (e.g., glasses, monoliths, dental implants, prostheses, and the like).

The term sol-gel film then is intended to encompass any type of ceramic coating that is formed (or is produced on a substrate surface) through the standard sol-gel methods described below and that is cured or adhered to a hard surface substrate through exposure to low temperatures (e.g., at most 800° C., preferably at most 700° C.). Thus, such a term does not encompass (specifically, though not solely) ceramic glazes that require high temperature curing for adhesion (e.g., 900° C. and above).

The term metal-containing (primarily) inorganic antimicrobial agent is intended to encompass any particulate formulation comprising a majority of a metal-based compound exhibiting excellent antimicrobial characteristics, even after being subjected to the high temperatures required for curing and setting of the target sol-gel film to the target hard surface substrate. Such a metal-based compound is preferably primarily inorganic in nature (some organic component is permitted, although the primary antimicrobial portion must be inorganic, in order to withstand the aforementioned high temperatures), is a solid at standard temperature and pressure, and which exhibits antimicrobial activity. Preferably, such material is a metal oxide, such as silver oxide, zinc oxide, and the like, a metal-containing (preferably silver-containing) ion-exchange compound, a metal-containing (preferably silver-containing) zeolite, or a metal-containing (preferably silver-containing) glass, and any combinations thereof. Alternatively, inorganic/organic hybrid-based metal antimicrobials, as one non-limiting example, silver sulfadiazine, may be utilized for such purpose either alone or in combination with other metal-containing antimicrobials as well. The preferred metal-containing ion exchange material is an antimicrobial silver zirconium phosphate available from Milliken & Company, under the tradename ALPHASAN®. Other potentially preferred silver-containing solid inorganic antimicrobials in this invention is a silver-substituted zeolite available from Sinanen under the tradename ZEOMIC®, or alternatively marketed under the tradename Aglon® by the company of the same name, or a silver-substituted glass available from Ishizuka Glass under the tradename IONPURE®, may be utilized either in addition to or as a substitute for the preferred species. Other possible compounds, again without limitation, are silver-based materials such as MICROFREE®, a mark denoting products developed by DuPont, as well as JMAC®, available from Johnson Mathey. Also available are compounds, such as silver sulfadiazine, which are generally organic in nature but provide excellent antimicrobial activity and can withstand high sintering temperatures in certain applications. Generally, such a metal-based inorganic antimicrobial agent compound is added (and thus is present) within the sol-gel film precursor formulation added in an amount of from about 0.00001 to 10% by total weight of the precursor composition; preferably from about 0.001 to about 5%; more preferably from about 0.01 to about 1%; and most preferably from about 0.1 to about 1.0%.

As one preferred embodiment, in comparison with the simpler structures such as silver oxide particles, inventive films comprising such ion-exchange or zeolite compounds appear to provide more durable antimicrobial levels, particularly when coated hard surface substrates are subjected to highly caustic cleaning preparations, and do not exhibit discoloration over time.

Other possible components within the inventive films include antistatic compounds, fillers, such as calcium carbonate (to provide strength and hardness to the film), flame retardants, such as antimony oxide, available from Great Lakes Chemical, and dyes and other colorants to impart desirable colorations therein.

The production of film materials by the sol-gel process has been known for many years. A "sol" is a dispersion of colloidal particles in a liquid, and the term "gel" connotes an interconnected, rigid network with pores of submicrometer dimensions and polymeric chains whose average length is greater than a micrometer. Basically, the film-forming sol-gel process involves mixing of host precursors (e.g., alkyl metal oxides, as discussed in greater detail below) and any additives into a sol; applying the sol to a selected surface; gelation of the mixture, whereby the colloidal particles link together to become a porous three-dimensional network in film form; aging of the gel to increase its strength; drying the liquid from the interconnected pore network within the film; dehydration or chemical stabilization of the pore network; and densification, to produce structures with ranges of physical properties. As background, one can review, e.g., Hench & West, The Sol-Gel Process, 90 Chem. Rev. 33 (1990).

All of these steps can generally be carried out at relatively low temperatures, as compared with traditional glassmaking techniques, as well as typical glazing techniques for ceramics (as noted in U.S. Pat. No. 5,882,808, above). Using the procedures described herein below, the inventive antimicrobial sol-gel films can be prepared from gels by sintering between 300 and 800° C., well below the temperatures required for glassmaking and glazing. Accordingly, these procedures afford cost-effective production for preparing effective antimicrobial hard surface substrates.

Such a sol-gel process also permits use of very small colloidal particles (on the order of one nanometer or less) as glass precursors, thereby ensuring a high degree of homogeneity and purity in the final film product. The films of the present invention are prepared from any number of base host precursors, including, without limitation, alkoxysilanes, preferably tetramethoxysilane ("TMOS"), tetraethoxysilane ("TEOS"), and the like, as well as acetylacetonates, such, again, without limitation, titanium acetylacetonate, zirconium acetylacetonate, and aluminum acetylacetonate. Such host precursors were then converted to the metal oxide through standard sol-gel preparation techniques, namely and preferably (without limitation) through addition (in solid form, e.g., powder, particulate, and the like) to a heated mixture of acetic acid and methanol. Added simultaneously or pre-mixed with the solid host precursor are particles or powders of the desired antimicrobial component as noted above, the resultant composition of which is then mixed and heated. The mixture can then be sonicated or like treated and applied to the desired hard substrate surface through any standard type of application, such as, without limitation, drip coating, immersion, spraying, and the like. The coated substrate can then be fired (such as within a kiln) in order to set and solidify the desired sol-gel film thereto.

More specifically, then, the sol-gel film producing process entails the conversion of a sol component to a gel component which can then be heated to a sufficiently high temperature in order to generate the desired film. The sol generally consists of metal alkoxide in the presence of water. Such a component then undergoes hydrolysis to form the correlated metal hydroxide species. Condensation of two metal hydroxides then combine such species to form a single (di)metal oxide (with water released in such a reaction). More and more metal oxides form together and increase in molecular weight to form a three-dimensional network, particularly in the presence of a necessary solvent to liquefy the sol to the extent that gel formation is permitted. The sol then becomes the desired three-dimensional gel composition. With regard to this invention, the inorganic antimicrobial may be introduced within the sol (metal alkoxide) initially and then applied, with the sol, to a hard surface substrate prior to gel formation, at which point the gel can be formed with the antimicrobial present therein creating an antimicrobial film on the target hard surface substrate after exposure to sufficient heat for sintering of the film to the surface. Alternatively, the inorganic antimicrobial component may be combined with the initial sol component, for further gel formation therewith, after which the solvent within the gel is then removed. After solvent removal, the resultant friable gel can then be ground into a powder that can be resuspended with addition of solvent thereto. Sintering of the resultant dispersion can then be easily performed to provide the desired hard surface substrate. Thus, this invention permits unique flexibility in providing antimicrobial low-temperature films for hard surface substrates.

The inventive films are thus produced through the initial compounding of the base compounds together, or providing a powder which can be modified to a gel upon introduction of solvents, and drying to form a film precursor formulation (e.g., gel) exhibiting a certain degree of adhesiveness or tackiness. This precursor formulation can then be applied through coating procedures, sprayings, immersions, or any like process, to the target hard surface substrate after which the coated substrate is then exposed to a sufficiently high temperature to effectuate the substantially uniform film production over the coated portion of the substrate. The desired antimicrobial agents, as discussed above, are thus added prior to the formation of the film precursor formulation and are present within such a coated formulation during the heating step. The resultant inventive film, and thus the resultant coated hard surface substrate, exhibits excellent antimicrobial properties, again, as discussed above and further presented within the preferred embodiments provided below. Adding such solid antimicrobial agents after film production is extremely difficult without the production of highly undesirable discolorations (e.g., darkening, particularly due to the high temperatures utilized for film formation).

The particular metal-based antimicrobial agent (e.g., silver-containing inorganic antimicrobial compound) should exhibit an acceptable log kill rate after 24 hours in accordance with the above-noted modified plate contact method. Such an acceptable level log kill rate is tested for *Klebsiella pneumoniae* (as well as for *Staphylococcus aureus*, *Escherichia coli*, and any other standard, commonly found bacteria; for test purposes, the results for *K. pneumoniae* are used most prominently) of at least 0.1 increase over baseline (with at least a log kill rate of 0.5 and above, preferred). Alternatively, an acceptable level will exist if the log kill rate is greater than the log kill rate for non-treated (i.e., no solid inorganic antimicrobial added) films (such as about 0.5 log kill rate increase over control, antimicrobial-free latices). Preferably this log kill rate baseline increase is at least 0.3 and 0.3, respectively for *S. aureus* and *K. pneumoniae;* more preferably these log kill rate is 0.5; and more preferably is 1.0, respectively. Of course, the high end of such log kill rates are much higher than the baseline, on the magnitude of 5.0 (99.999% kill rate). Any rate in between is thus, of course, acceptable as well. In such an instance, the antimicrobial material present within the films at least exhibits a hindrance to microbe growth.

DESCRIPTION OF PREFERRED EMBODIMENTS

Examples of particularly preferred compounds within the scope of the present invention are set forth below.

Film Precursor Formulation Production

The preferred inventive sol-gel films were produced in accordance with the compositions denoted within the Table below with all of the components admixed together. The basic procedure entailed the production of preferred alumina oxide, titania oxide, zirconia oxide, or silica oxide host thin films via sol-gel processes. Thus, initially about 5 g of a host precursor component selected from the preferred, non-limiting group of either aluminum acetylacetonate, titanium acetylacetonate, zirconium acetylacetonate, was added to a mixture of 20 g of acetic acid and 10 g (28%) methanol (which have already been heated and stirred at 65° C. for 15 minutes). The powder was then added with 2% (of the total weight of metal components within the host precursor) of either silver oxide (available from Aldrich under catalog #22,683-1), RC 5000 (an ALPHASAN® antimicrobial available from Milliken & Company), IONPURE®, silver sulfadiazine, or ZEOMIC®, to the acid/methanol mixture. The resultant mixture was then heated at 65° C. and stirred for an additional 15 minutes. For TMOS host precursors, the sol was prepared by adding from 5–10% by weight of methanol, as well as 2% of the antimicrobial agent in powder form (as defined above) to the TMOS liquid composition and stirring the resultant formulation at 65° C. for 15 minutes. Subsequently, for either acetylacetonate or TMOS host precursor formulations, the resultant composition was sonicated for 15 minutes and applied to the target hard surface substrate (noted below) through drip coating while maintaining the same temperature as before. The coated substrate was then fired in a kiln at a ramp of 2° C. until the desired high temperature (300, 500, or 700° C., as noted below) was reached. Upon reaching such a high temperature, the substrate remained exposed at the same high temperature for a 30 minute dwell time. The substrate was then removed and tested for antimicrobial activity, both directly after cooling as well as after exposure to a caustic solution at elevated temperature (about 50° C.) for 48 hours. The components, firing temperatures, substrates (being either 1 inch by 1 inch ceramic tiles (available from the Tile Council of America), 0.5 inch by 0.5 inch polyimide films (KAPTON®) from DuPont), or 1 inch by 1 inch silica tiles (portions of borosilicate microscope slides, catalog #12-549 from Fisher Scientific) as non-limiting substrate examples), are listed below, followed by the antimicrobial test results for such substrates:

TABLE

Components, Etc., of Test Film Coatings

| Ex. # | Substrate | Firing Temp. (° C.) | Antimicrobial | Host Precursor |
|---|---|---|---|---|
| 1 | Ceramic | 300 | RC 5000 | Ti acetylacetonate |
| 2 | Ceramic | 500 | RC 5000 | Ti acetylacetonate |
| 3 | Ceramic | 700 | RC 5000 | Ti acetylacetonate |
| 4 | Ceramic | 300 | Silver Oxide | Ti acetylacetonate |
| 5 | Ceramic | 500 | Silver Oxide | Ti acetylacetonate |
| 6 | Ceramic | 700 | Silver Oxide | Ti acetylacetonate |
| 7 | Ceramic | 300 | RC 5000 | Al acetylacetonate |
| 8 | Ceramic | 500 | RC 5000 | Al acetylacetonate |
| 9 | Ceramic | 700 | RC 5000 | Al acetylacetonate |
| 10 | Ceramic | 300 | Silver Oxide | Al acetylacetonate |
| 11 | Ceramic | 500 | Silver Oxide | Al acetylacetonate |
| 12 | Ceramic | 700 | Silver Oxide | Al acetylacetonate |
| 13 | Ceramic | 500 | RC 5000 | TMOS |
| 14 | Ceramic | 700 | RC 5000 | TMOS |
| 15 | Ceramic | 500 | Silver Oxide | TMOS |
| 16 | Ceramic | 700 | Silver Oxide | TMOS |
| 17 | Polyimide | 300 | RC 5000 | Zr acetylacetonate |
| 18 | Polyimide | 300 | Silver Oxide | Zr acetylacetonate |
| 19 | Polyimide | 300 | IONPURE | Zr acetylacetonate |
| 20 | Polyimide | 300 | ZEOMIC | Zr acetylacetonate |
| 21 | Polyimide | 300 | Silver sulfadiazine | Zr acetylacetonate |
| 22 | Silica | 500 | RC 5000 | TMOS |
| 23 | Silica | 500 | Silver Oxide | TMOS |
| 24 | Silica | 300 | Silver Oxide | Ti acetylacetonate |
| 25 | Silica | 500 | Silver Oxide | Zr acetylacetonate |
| 26 | Silica | 500 | IONPURE | Zr acetylacetonate |
| 27 | Silica | 300 | Silver Oxide | Zr acetylacetonate |
| 28 | Silica | 300 | IONPURE | Zr acetylacetonate |
| 29 | Silica | 300 | RC 50000 | Zr acetylacetonate |
| 30 | Silica | 300 | Silver Sulfadiazine | Zr acetylacetonate |
| 31 | Silica | 300 | ZEOMIC | Zr acetylacetonate |
| 32 | Silica | 300 | Silver Oxide | Ti acetylacetonate |

After production of such film-coated hard surface substrates, the substrates were then tested for antimicrobial activity via a plate-contact method (modified JIS Z 2801:2000). Basically, such a test protocol required immersion of the plate (substrate) within in a solution comprising 0.4 mL of $1 \times 10^5$ of cells/mL of *Klebsiella pneumoniae* ATCC #4352 bacteria for 22 hours in a Na/K phosphate buffer solution. The number of killed cells was then calculated and recorded as the log kill rate after this 22 hour exposure test. The results are as follows in tabular form:

TABLE 1

EXPERIMENTAL DATA
Log Kill Rates for *K. pneumoniae*

| Ex. # | Log Kill Rate for *K. pneumoniae* |
|---|---|
| 1 | 3.4 |
| 2 | 3.2 |
| 3 | 3.7 |
| 4 | 3.4 |
| 5 | 3.4 |
| 6 | 3.5 |
| 7 | 3.4 |
| 8 | 3.7 |
| 9 | 3.7 |
| 10 | 3.7 |
| 11 | 3.2 |
| 12 | 3.5 |
| 13 | 2.55 |
| 14 | 0.60 |
| 15 | 1.95 |
| 16 | 2.55 |
| 17 | 2.33 |
| 18 | 2.33 |
| 19 | 2.33 |
| 20 | 2.33 |
| 21 | 2.33 |
| 22 | 2.50 |
| 23 | 1.95 |
| 24 | 1.70 |
| 25 | 1.25 |
| 26 | 1.95 |
| 27 | 3.40 |
| 28 | 3.40 |
| 29 | 3.40 |
| 30 | 3.40 |
| 31 | 3.40 |
| 32 | 1.75 |

Two samples, 13 and 15, were then subjected to an incubation procedure at room temperature (e.g., about 20–25° C.) within a 30% aqueous ammonia bath for about 15 hours, washed with tap water, and then dried in an oven at 110° C. for another 15 hours. Alternatively, other samples of the same type were also incubated within a 1% aqueous sodium hydroxide bath (instead of the ammonia bath, above) under the same washing and drying conditions as above. Such tests were intended to show the ability of the substrates to exhibit durable antimicrobial properties after exposure to pH levels of common cleaning treatments (in this test, both baths are exhibit a pH of about 12). The antimicrobial activity (via the film-contact method above) and empirical analysis of the color of the substrates subsequent to such caustic treatments were then taken (no discoloration indicates acceptable levels; any discolorations indicate unacceptable for aesthetic purposes). The results are below in tabulated form:

TABLE 2

EXPERIMENTAL DATA
Log Kill Rates for *K. pneumoniae* and Discoloration Analyses

| Ex. # | Bath Type | Log Kill Rate for *K. pneumoniae* | Discoloration? |
|---|---|---|---|
| 13 | Ammonia | 3.7 | none |
| 13 | NaOH | 3.7 | none |
| 15 | Ammonia | 2.6 | Light pink |
| 15 | NaOH | 2.4 | Light pink |

Thus, the inventive adhesive sol-gel films and coated substrates exhibit excellent antimicrobial properties and durable properties as well. Furthermore, the silver-containing ion-exchange compounds also provide excellent durability as well as low levels of discoloration after caustic treatments. Thus, aesthetically pleasing, antimicrobial substrates may be provided via low-temperature sol-gel processes.

There are, of course, many alternative embodiments and modifications of the present invention which are intended to be included within the spirit and scope of the following claims.

What we claim is:

1. An antimicrobial sol-gel film comprising at least one silver-containing inorganic antimicrobial agent, wherein said film exhibits a log kill rate for *Klebsiella pneumoniae* of at least 0.5 as measured under a modified plate contact method, and wherein said film is capable of adherence to a hard surface substrate at a temperature of between 100° C. and 800° C.

2. The antimicrobial sol-gel film of claim 1 wherein said film exhibits a log kill rate for *Klebsiella pneumoniae* of at least 1.0.

3. The antimicrobial sol-gel film of claim 2 wherein said film exhibits a log kill rate for *Klebsiella pneumoniae* of at least 2.0.

4. The antimicrobial sol-gel film of claim 3 wherein said film exhibits a log kill rate for *Klebsiella pneumoniae* of at least 3.0.

5. The antimicrobial sol-gel film of claim 4 wherein said film exhibits a log kill rate or *Klebsiella pneumoniae* of at least 3.5.

6. The antimicrobial sol-gel film of claim 1 wherein said film is capable of adherence to a hard surface substrate at a temperature of between 300° C. and 800° C.

7. A hard surface substrate to which a sol-gel film has been applied over at least a portion of the surface thereof at a temperature of between 100° C. and 800° C., wherein the sol-gel film contains at least one sliver-containing inorganic antimicrobial agent, and wherein said film-coated hard surface substrate exhibits a log kill rate for *Klebsiella pneumoniae* of at least 0.5, as measured under a modified plate contact method, at said portion to which said sol-gel film has been applied.

8. The hard surface substrate of claim 7 wherein said film-coated hard surface substrate exhibits a log kill rate for *Klebsiella pneumoniae* of at least 1.0 at said portion to which said sol-gel film has been applied.

9. The hard surface substrate of claim 7 wherein said film-coated hard surface substrate exhibits a log kill rate for *Klebsiella pneumoniae* of at least 2.0 at said portion to which said sol-gel film has been applied.

10. The hard surface substrate of claim 7 wherein said film-coated hard surface substrate exhibits a log kill rate for *Klebsiella pneumoniae* of at least 3.0 at said portion to which said sol-gel film has been applied.

11. The hard surface substrate of claim 7 wherein said film-coated hard surface substrate exhibits a log kill rate for *Klebsiella pneumoniae* of at least 3.5 at said portion to which said sol-gel film has been applied.

12. The hard surface substrate of claim 9 exhibiting the same log kill rate after said film-coated substrate has been immersed in a heated caustic bath, having a pH level of at least 12, for 48 hours.

13. The hard surface substrate of claim 10 exhibiting the same log kill rate after said film-coated substrate has been immersed in a heated caustic bath, having a pH level of at least 12, for 48 hours.

14. The hard surface substrate of claim 11 exhibiting the same log kill rate after said film-coated substrate has been immersed in a heated caustic bath, having a pH level of at least 12, for 48 hours.

15. A hard surface substrate to which a sol-gel film has been applied over at least a portion of the surface thereof at a temperature of between 300° C. and 800° C., wherein the sol-gel film contains at least one silver-containing inorganic antimicrobial agent, and wherein said film-coated hard surface substrate exhibits a log kill rate for *Klebsiella pneumoniae* of at least 0.5, as measured under a modified plate contact method, at said portion to which said sol-gel film has been applied.

* * * * *